United States Patent [19]
Wang

[11] Patent Number: 5,282,483
[45] Date of Patent: Feb. 1, 1994

[54] MULTI-FUNCTION ADJUSTABLE IMMOBILIZING APPARATUS

[76] Inventor: Tzu-Chiang Wang, 1446 Sugar Creek Blvd., Sugar Land, Tex. 77478

[21] Appl. No.: 911,935

[22] Filed: Jul. 10, 1992

[51] Int. Cl.⁵ .............................. A61F 5/37; A61F 5/00
[52] U.S. Cl. ...................................... 128/882; 602/23; 602/27
[58] Field of Search ................ 602/4, 5, 6, 20, 21, 602/22, 23, 27; 128/878, 879, 880, 881, 882

[56] References Cited

U.S. PATENT DOCUMENTS

| | | | |
|---|---|---|---|
| 2,237,252 | 4/1941 | Longfellow | 602/20 |
| 2,646,794 | 7/1953 | Baer | 602/22 |
| 3,011,171 | 12/1961 | Pell | 602/22 |
| 3,101,812 | 4/1992 | Wang | 602/22 |
| 3,568,671 | 3/1971 | Graham | 602/23 |
| 3,776,225 | 12/1973 | Lonardo | 602/21 |
| 4,366,812 | 1/1983 | Nuzzo | 602/22 |
| 4,641,639 | 2/1987 | Padilla | 602/23 |
| 4,960,114 | 10/1990 | Dale | 602/21 |
| 4,977,890 | 12/1990 | Mann | 602/21 |
| 4,981,132 | 1/1991 | Chong | 602/23 |

Primary Examiner—Michael A. Brown
Attorney, Agent, or Firm—Cushman, Darby & Cushman

[57] ABSTRACT

An immobilizing apparatus for an injured body part includes a rigid plate conforming to the injured body part and having two opposite faces, upon one of which the injured body part is provided; a limiting unit to limit the lateral movement of the injured body part on the rigid plate; an adjustable member by which the overall length of the rigid plate can be adjusted; and a fastening member to fasten the injured body part, immobilizing the injured body part on the rigid plate.

2 Claims, 8 Drawing Sheets 5,282,483

MULTI-FUNCTION ADJUSTABLE IMMOBILIZING APPARATUS

BACKGROUND OF THE INVENTION

1. Field of Invention

This invention relates to an immobilizing apparatus, more particularly to a multi-function, reusable and adjustable immobilizing apparatus for an injured body part.

2. Description of the Related Art

In a conventional method of treatment for an injured body part, the site of the injured part is immobilized by applying a plurality of layers of plaster of Paris. The injured part will recuperate after a period of time.

The above-mentioned method, though quite beneficial, still has some problems. The injured person can not bathe as he normally would since the plaster of Paris will soften when exposed to water. The injured person also needs to carry a heavily weighted plaster device which is very inconvenient to the injured person.

SUMMARY OF THE INVENTION

A main object of the present invention is to provide an adjustable and re-usable apparatus for immobilizing an injured body part so that the injured part will recuperate as if it were immobilized by applying plaster of Paris.

According to the present invention, an adjustable, re-usable and multi-function immobilizing apparatus for an injured body part includes an elongated rigid plate conforming to the injured body part and having two opposite faces on which the injured body part is placed and two longitudinal edges, the elongated rigid plate further having limiting means to limit the lateral movement of the injured body part; an adjustable member disposed on the elongated rigid plate, by the aid of which the overall length of the rigid plate can be adjusted; and strap means for fastening the site of injury on the rigid plate and simultaneously immobilizing the site of injury. A distinguishing feature is that it can be employed on a body part wherever the injury may be, and since the overall length of the apparatus is adjustable, it can be used on young people or adults.

BRIEF DESCRIPTION OF THE DRAWINGS

Other features and advantages of the present invention will become more apparent in the following detailed description, including drawings, all of which show a non-limiting form of the present invention, and of which.

DETAILED DESCRIPTION OF THE PREFERRED EMBODIMENT

An immobilizing apparatus for an injured body part according to the present invention includes an elongated rigid plate conforming to the injured body part and having two opposite faces upon one of which the injured body part is placed, and two longitudinal edges; means for limiting the lateral movement of the injured body part on the elongated rigid plate, which movement is transverse to and between the two longitudinal edges of the elongated rigid plate; an adjustable member for adjusting an overall length of the rigid plate so that it can accommodate the site of injury; and strap means for fastening the injured body part, thereby immobilizing the injured body part on the rigid plate.

Figure 1:
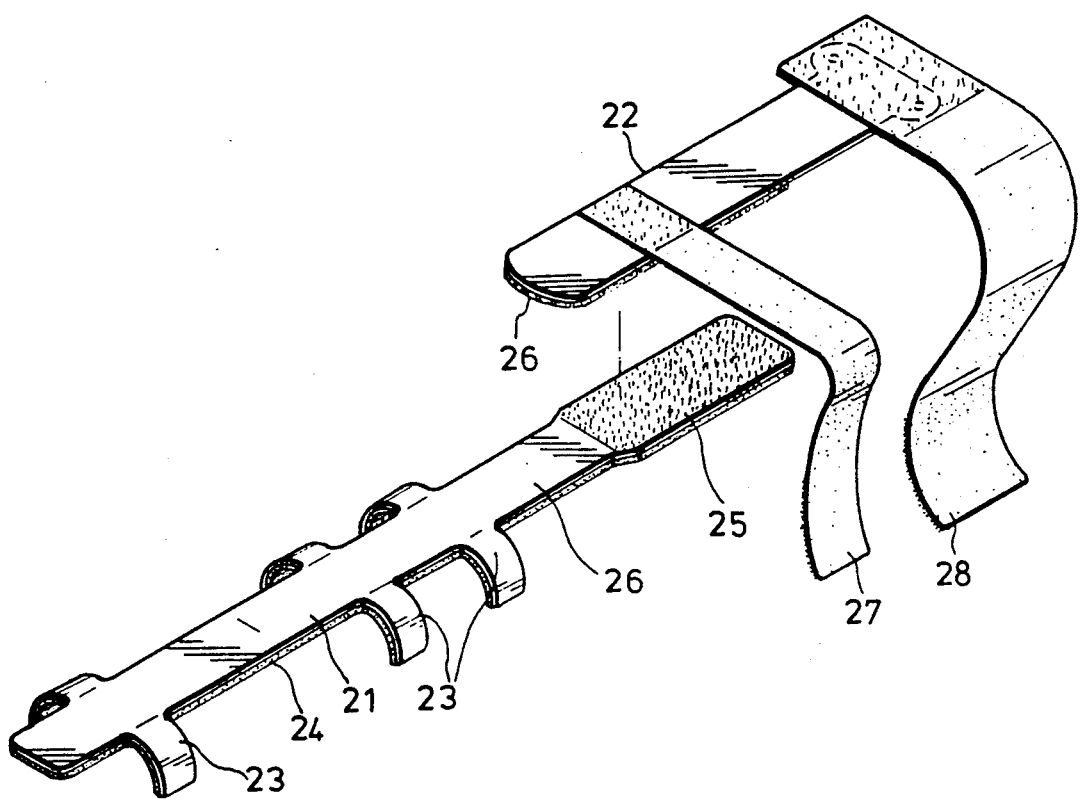
FIG. 1 shows a first preferred embodiment of a apparatus for immobilizing an injured body part according to the present invention.
Figure 2:
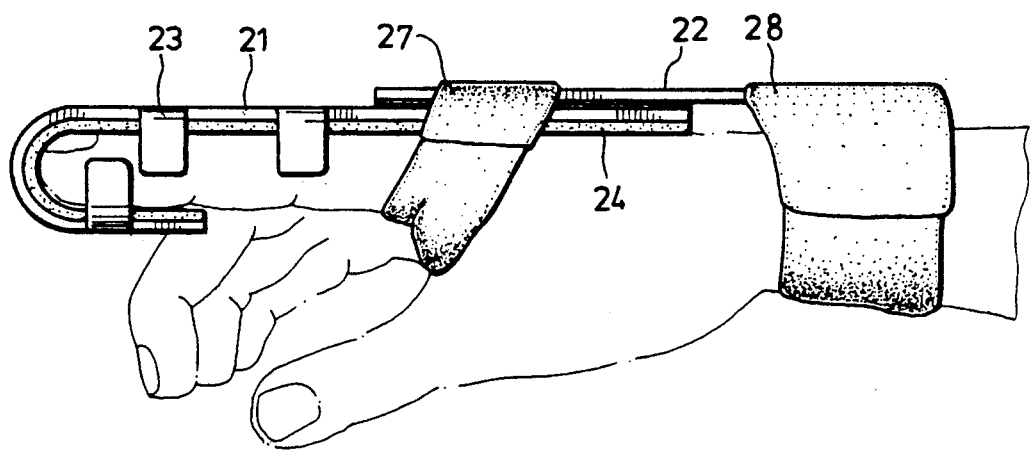
FIG. 2 shows the immobilizing apparatus of FIG. 1 in application.

Referring to FIG. 1, the injured body part is a finger. Therefore, the elongated rigid plate of the preferred embodiment includes a first elongated aluminum plate (21) having two longitudinal edges. The adjustable means includes a second elongated aluminum plate (22) detachably connected to the first plate so as to adjust an overall length of the first plate and two VELCRO fasteners (25,26), one disposed on the first plate (21) and the other disposed on the second plate (22). The limiting means includes a plurality of aluminum studs (23) integrally formed with and laterally extending from two longitudinal peripheral edges of the first plate (21) and bendable relative to the same so that it can shield and limit a lateral movement of the finger between the longitudinal peripheral edges of the first plate (21). The strap means includes an elongated first VELCRO fastener (27) fastening the finger to the first plate, thus immobilizing the same, and a second VELCRO fastener (28) retaining the wrist to the second plate (22). A soft cushioning stack (24) can be disposed between the finger and the first plate to cushion the finger, as shown in FIG. 2.

Figure 3:
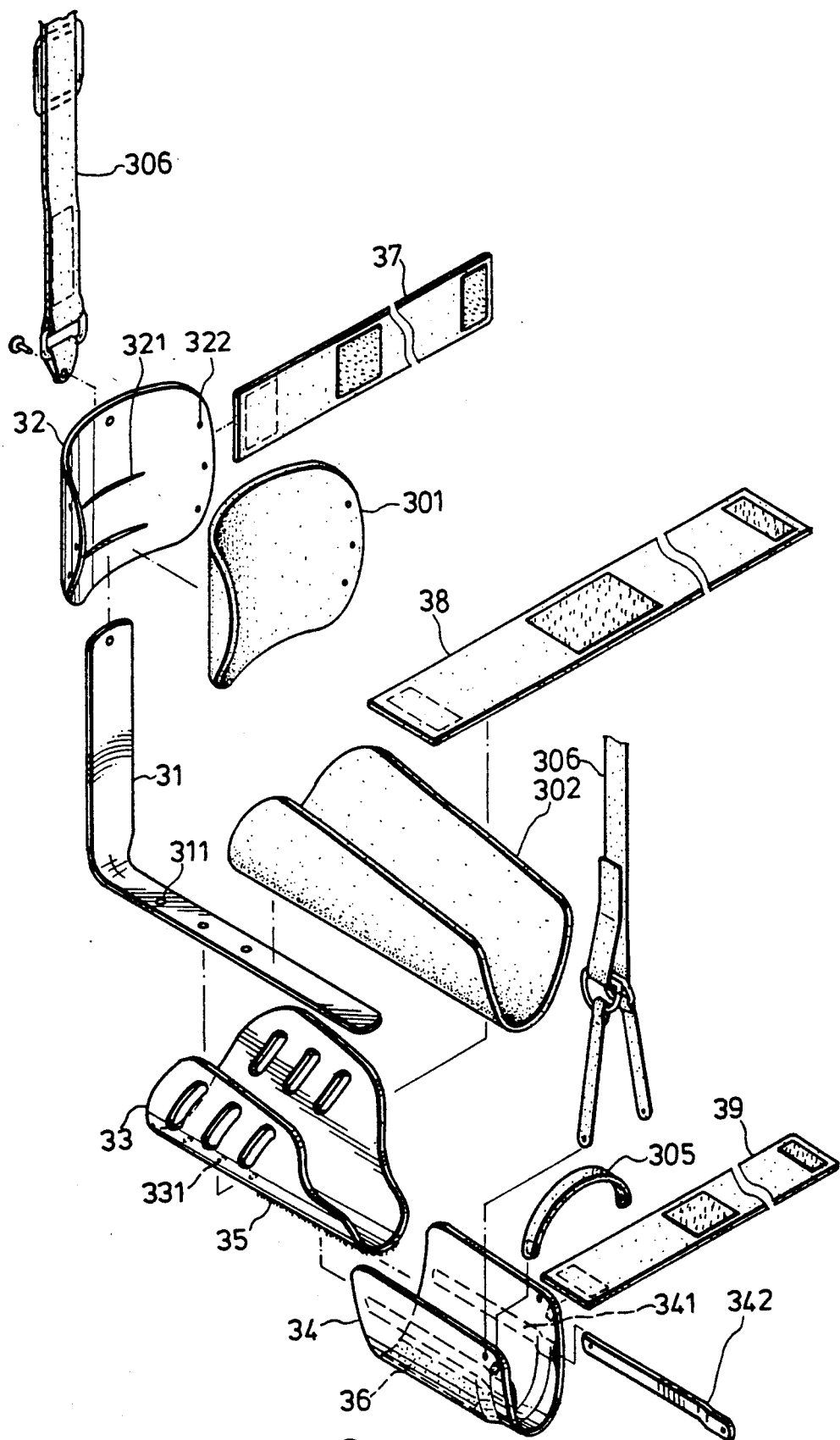
FIG. 3 shows an exploded view of a second preferred embodiment of an apparatus for immobilizing an injured body part according to the present invention.
Figure 4:
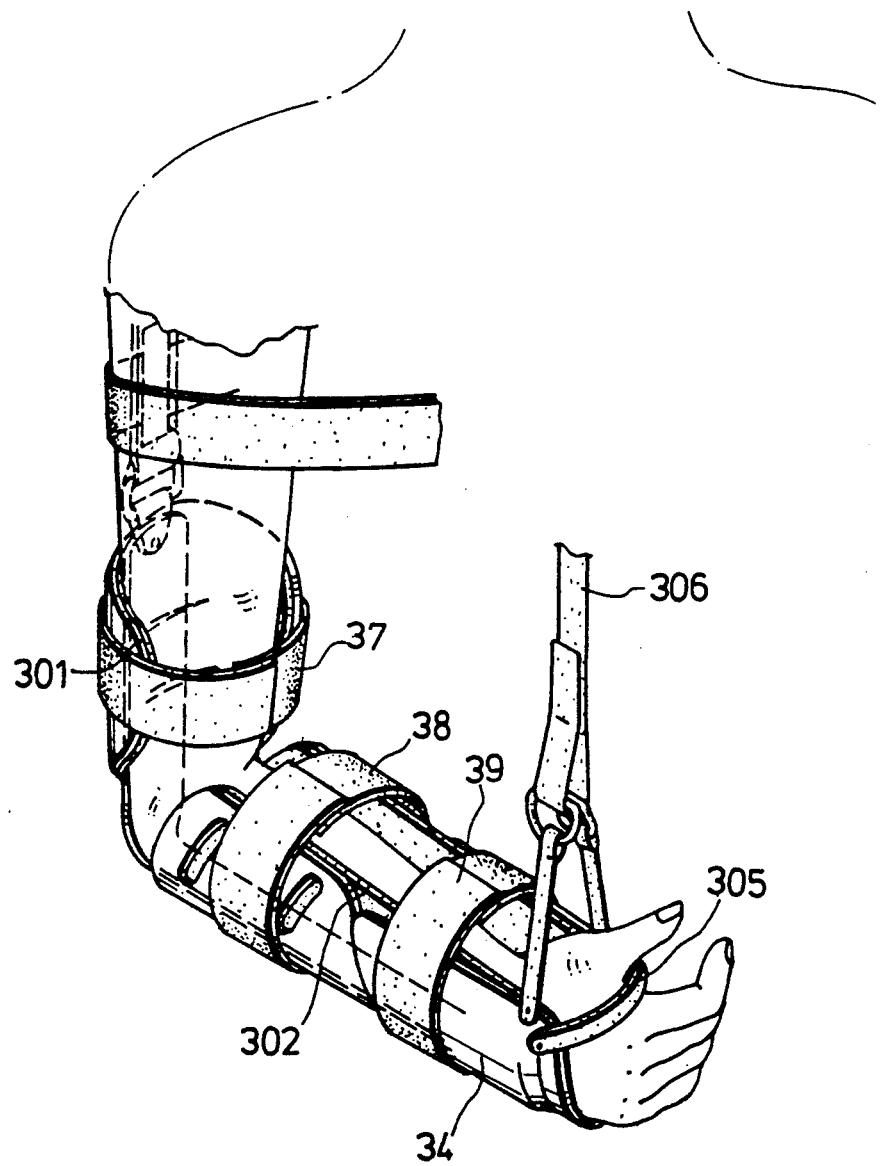
FIG. 4 shows the immobilizing apparatus of FIG. 3 in application.

Referring to FIGS. 3 and 4, if the injured body part is an arm, the rigid plate can be made to have an L-shaped plate (31) that includes a plurality of mounting holes (311). The limiting means includes a first flexible support member (32), an inner face of which has engaging projections (321) to engage with an outer face of the L-shaped plate, the vertical movement of the first support member (32) allowing the adjustment of this portion to fit different arm lengths, of the arm, a second flexible support member (33) and a third flexible support member (34). The second flexible support member (33) has a plurality of engaging projections (331) engaging in the mounting holes (311) of the L-shaped plate (31). It also has a VELCRO fastener (35) provided at an outer surface thereof and engageable with a VELCRO fastener (36) provided on the third flexible support member (34). The third flexible support member (34) has an elongated receiving space (341) to receive a preventive rod (342) which prevents the wrist of an injured forearm from bending inward as shown in FIG. 4. A first buffer cotton plate (301) can be attached to the first support member (32) with the rear section of the L-shaped plate being between the two elements, and a second buffer cotton plate (302) can be disposed on the second and third flexible support members (33,34) so the injured arm placed on the L-shape plate will be cushioned tenderly after it is immobilized by a plurality of VELCRO fasteners (37,38,39) fastened therearound. The injured part will recuperate faster if it is held stable by a hanging strap (306) as shown in FIG. 4.

Figure 5:
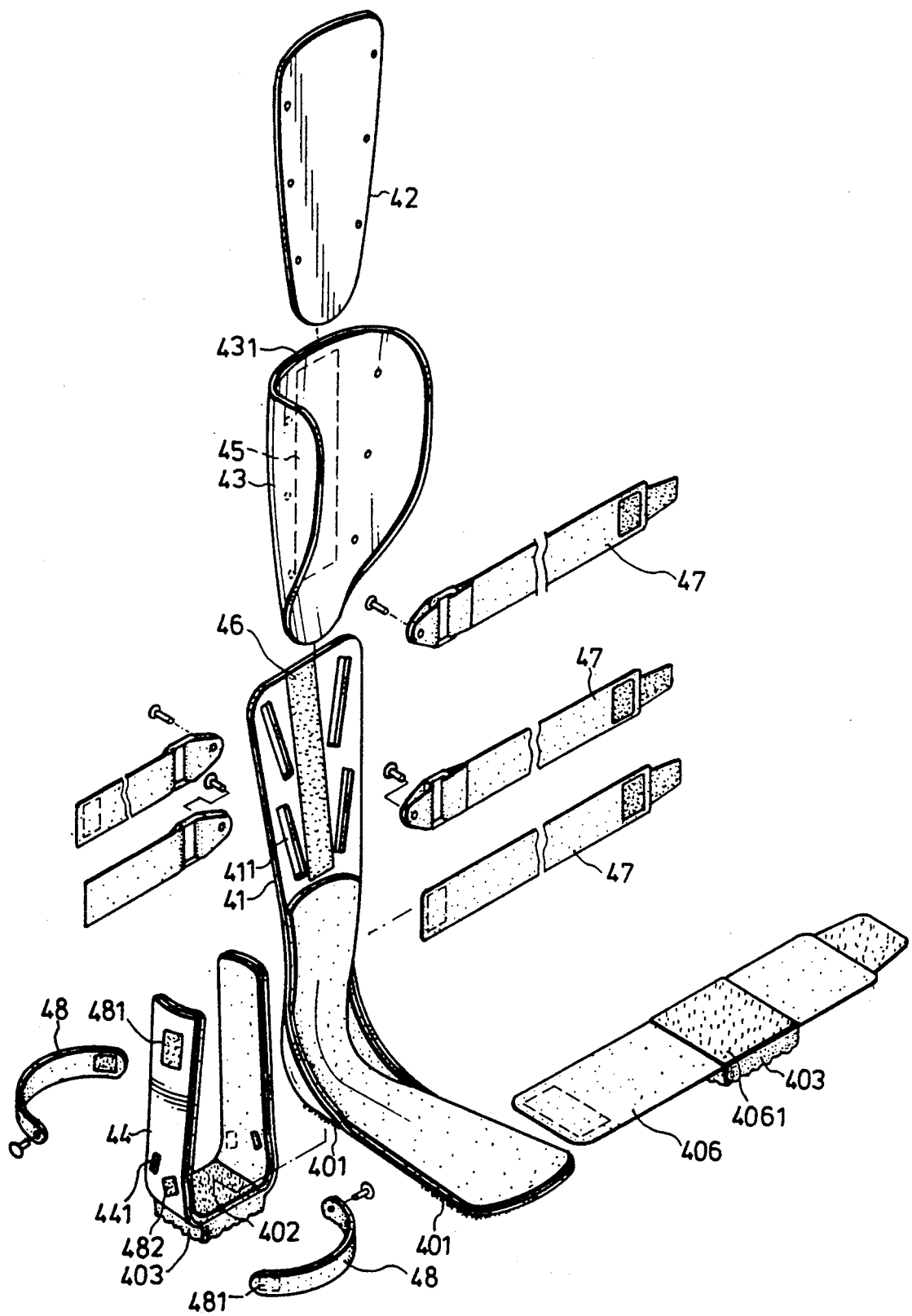
FIG. 5 shows an exploded view of a third preferred embodiment of an immobilizing apparatus of the present invention.
Figure 6:
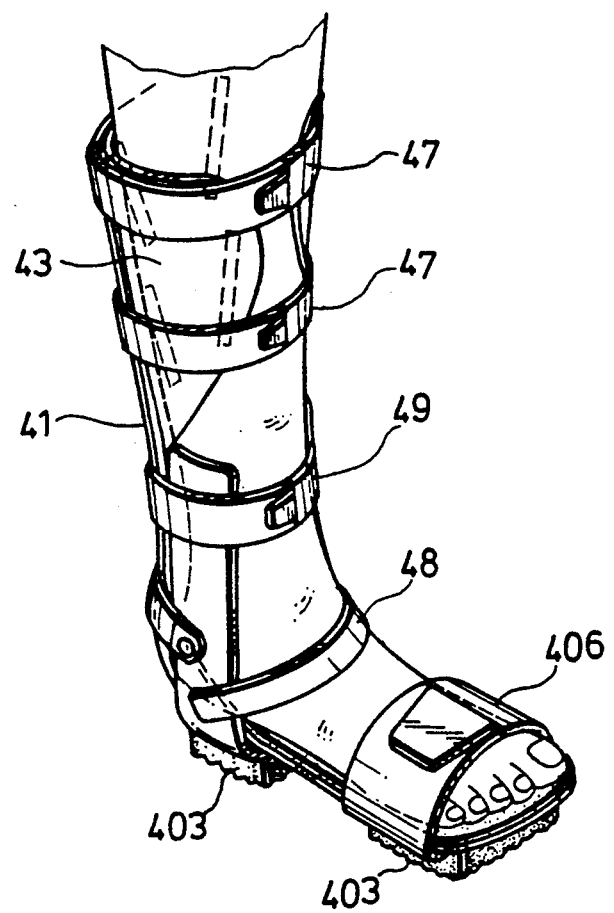
FIG. 6 shows the immobilizing apparatus of FIG. 5 in application.

FIG. 5 shows a preferred embodiment of an immobilizing apparatus of the present invention for use on an injured foot. As shown, it includes a substantially L-shaped plate (41) and an auxiliary part (42) which are made from a substantially hard material. The L-shaped plate (41) includes a first section and a second section integrally formed with the first section in addition to the formation of a predetermined angle between the first and second sections. The first section has an elongated first VELCRO fastener (46) extending longitudinally along the length thereof, two pairs of elongated slots (411), each pair placed on both sides of the elongated first VELCRO fastener (46), and two second VELCRO fasteners (401) at a bottom thereof. The limiting means is made from a soft material that includes a first flexible support member (43) which confines a receiving space (431) therein to receive the hard auxiliary part (42); a second flexible support member (44) having a support heel (403) at a bottom face, and a third VELCRO fastener (402) at an inner face and a second VELCRO fastener (482) at an outer face; and a third support member (406) with a support heel (403) and a fourth VELCRO fastener (4061) at an upper face. The first support member (43) has an elongated fifth VELCRO fastener (45) longitudinally disposed thereon which can be attached to the elongated first VELCRO fastener (46) of the L-shaped plate (41), thus making slight lengthening of the L-shaped plate possible. After the injured foot is placed on the L-shaped plate (41), a set of first fastening straps (47), each having two sections, adjustably engages at one end in the elongated first slot (411) of the L-shaped plate (41) by screw means while the other end encircles the leg to engage with another end of the remaining section. A second fastening strap (48) fastens the leg above the ankle. Since the second and third support members (44,406) each have their own fastening means (also VELCRO fastener), they also serve as a walking means in addition to fastening the ankle. Once the injured foot is thus immobilized on the L-shaped plate, it can recuperate after a given period of time.

Figure 7:
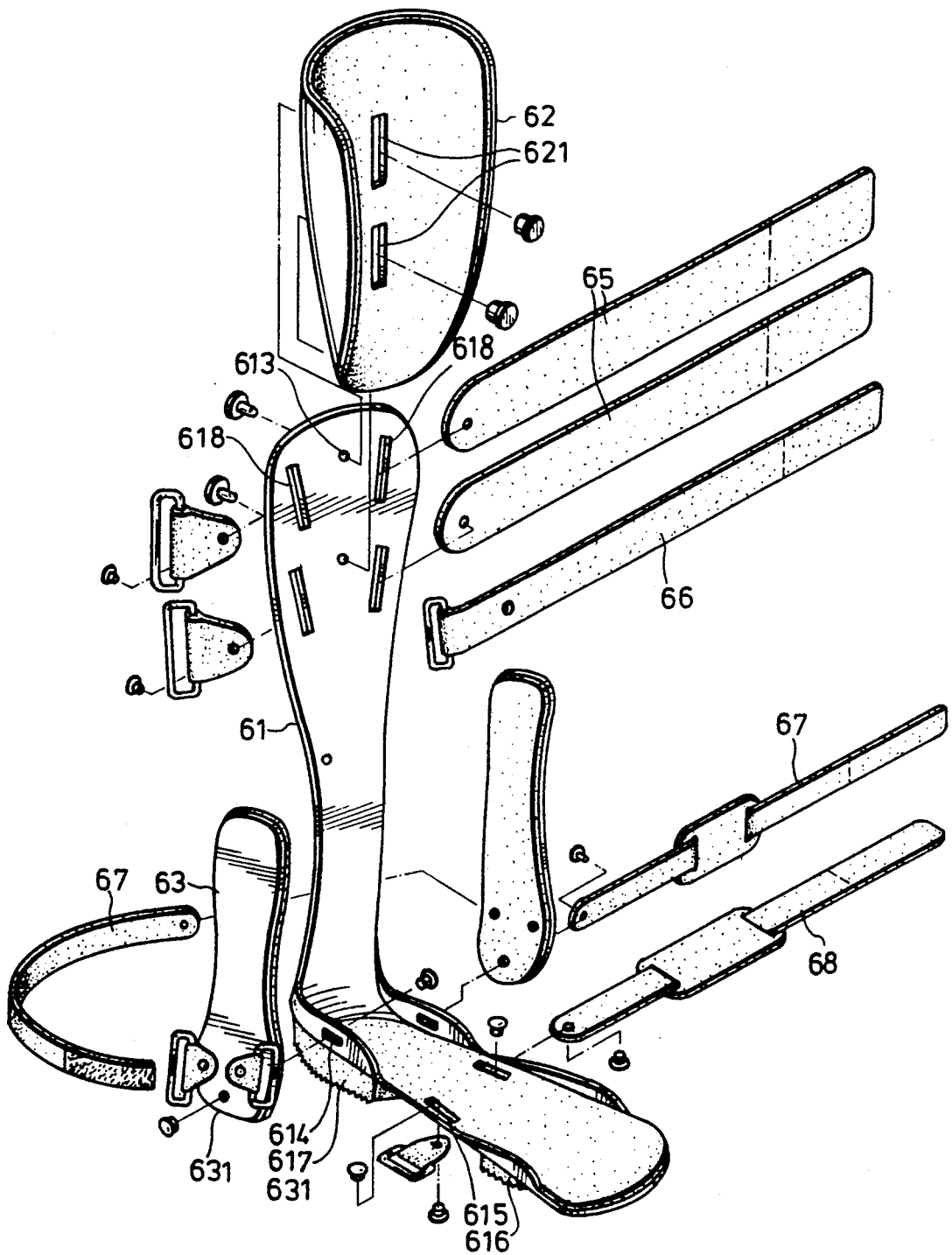
FIG. 7 shows an exploded view of a fourth preferred embodiment of an immobilizing apparatus of the present invention.
Figure 8:
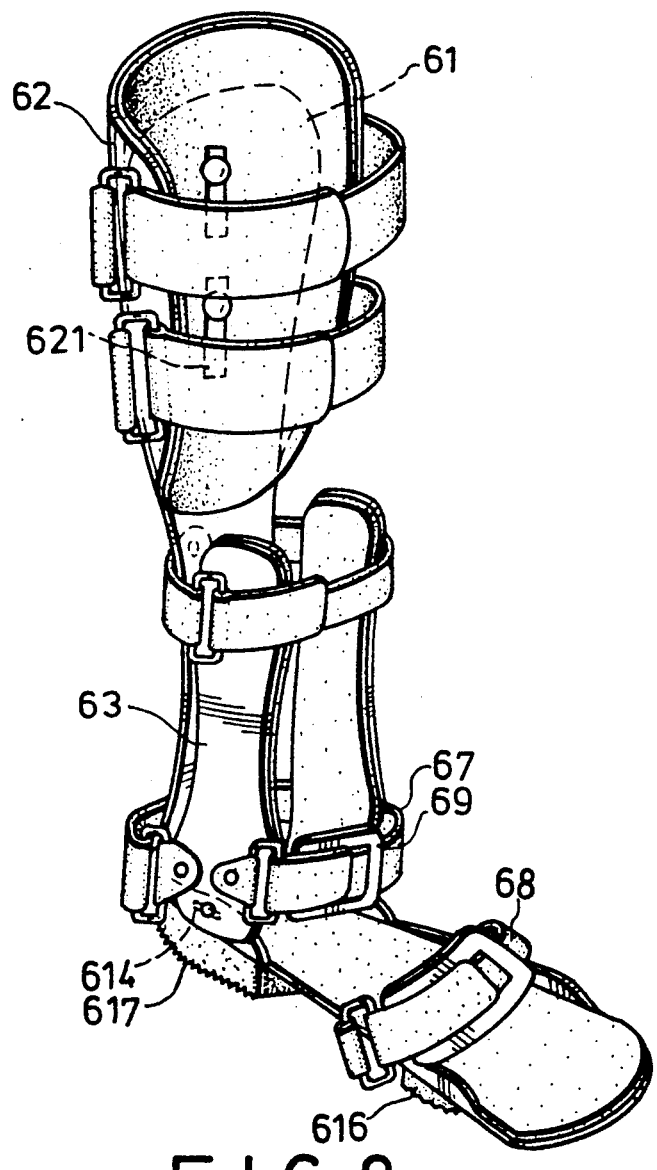
FIG. 8 shows the assembled view of the fourth preferred embodiment of FIG. 7.

Referring to FIG. 7, another embodiment of an immobilizing apparatus according to the present invention is shown to include an L-shaped plate (61) made of a substantially hard material which includes a first section which has a row of longitudinally aligned mounting holes (613) and a plurality of pairs of elongated second slots (618) disposed on both sides of the aligned mounting holes and a second section including a pair of elongated aligned third slots (614) and a pair of elongated fourth slots (615), as shown in FIG. 7. To match its particular structure, the limiting means of the preferred embodiment includes a first flexible support member (62) provided with two elongated fifth slots (621) which can adjustably engage with the L-shaped plate at the mounting holes (613) by screw-and-nut means and a second support member that includes a pair of elongated support plates (63), each of which has a second mounting hole (631) adjustably engaged to the elongated third slots (614) by screw-and-nut means. The fastening members (65,68) are buckle-and-strap types, and they include a first fastening member (65) adjustably engaging in the elongated second slots (618) on the first section of the L-shaped plate (61) to fasten the calf portion of the leg, a second fastening member (68) adjustably engaging in the elongated fourth slot (615) of the second section of the L-shaped plate (61) to fasten the toe portion of the leg and a third fastening member (67) adjustably engages in the elongated third slot (614) to secure around the ankle portion. The fastening members (66,67,69) are used to immobilize the lower leg and the ankle area. The feature and object of this embodiment are the same as that of the preceding embodiment. Since there are walking means (617,616) disposed at the bottom of the L-shaped plate, the patient can try walking after resting for a period of time.

While a preferred embodiment has been described and explained, it will be apparent that many changes and modifications may be made in the general construction and arrangement of the present invention without departing from the spirit and scope thereof. Therefore, it is desired that the present invention be limited not to the exact disclosure but only to the extent of the appended claims.

I claim:

1. A multi-function reusable and adjustable immobilizing apparatus for an injured leg, comprising:

an L-shaped rigid plate substantially conforming to said injured leg for receiving and limiting lateral movement thereof, having two opposite faces and two opposite longitudinal peripheral edges;

first and second portions integrally formed at a predetermined angle, said first portion having an elongated first hook and loop fastener strip extending longitudinally along the length thereof and a plurality of pairs of elongated first slots disposed on both sides of said first hook and loop fastener strip, said second portion having an elongated second hook and loop fastener strip disposed thereon;

means for limiting lateral movement transverse to and between said edges thereby confining said injured leg to a predetermined position on one of said opposite faces, having a first flexible support member with an elongated third hook and loop fastener strip longitudinally extending thereon adjustably and detachably attaching to said elongated first hook and loop fastener strip, a second flexible support member having a fourth hook and loop fastener strip detachably connecting said second hook and loop fastener strip of said second portion and extending from said second hook and loop fastener strip past the ankle of said injured leg; and means for securing said injured leg to said rigid plate having a mounting hole and a screw member extending into said mounting hole to adjustably engage said elongated first slot of said first portion.

2. A multi-function reusable and adjustable immobilizing apparatus for an injured leg, comprising:

an L-shaped rigid plate substantially conforming to said injured leg for receiving an limiting lateral movement thereof, having two opposite faces and two opposite longitudinal peripheral edges, a first and second portion integrally formed at a predetermined angle, said first portion having a row of longitudinally aligned holes and a plurality of pairs of elongated first slots, each pair of said first slots being disposed on both sides of said aligned holes and a pair of elongated second slots provided on a second portion;

means for limiting lateral movement transverse to and between said edges thereby confining said injured leg to a predetermined position on one of said opposite faces, having a first flexible support member with an elongated third slot to selectively register with one of said aligned holes whereby a first screw means passes through said third slot and said aligned hole to fasten said first support member and said first section, a second flexible support member having a first mounting hole and a second screw means passing through said first mounting hole thereby adjustably mounting to said elongated second slots of said second section and extending from the outer face of said rigid plate past the ankle of said injured leg; and means for securing said injured leg on said rigid plate, having a first strap member with a second mounting hole and a third screw means passing through said second mounting hole thereby adjustably attaching to said elongated second slots of said first portion, a second strap member with a third mounting hole and a fourth screw means passing through said third mounting hole thereby adjustably attaching to said elongated third slot of said second portion.

* * * * *